(12) United States Patent
Galloway, Jr. et al.

(10) Patent No.: US 8,558,046 B2
(45) Date of Patent: Oct. 15, 2013

(54) AROMATIC ALKYLATION PROCESS

(75) Inventors: Frederick Merrill Galloway, Jr., Tomball, TX (US); Ashim Kumar Ghosh, Houston, TX (US); Mohammad Shafiei, Sugar Land, TX (US); Peter N. Loezos, Houston, TX (US)

(73) Assignee: Saudi Basic Industries Corporation, Riyadh (SA)

(*) Notice: Subject to any disclaimer, the term of this patent is extended or adjusted under 35 U.S.C. 154(b) by 821 days.

(21) Appl. No.: 12/473,407

(22) Filed: May 28, 2009

(65) Prior Publication Data

US 2010/0305378 A1  Dec. 2, 2010

(51) Int. Cl.
*C07C 2/66* (2006.01)

(52) U.S. Cl.
USPC ........... 585/449; 585/435; 585/446; 585/467; 585/310; 585/319; 585/323; 585/804; 585/802; 585/805

(58) Field of Classification Search
USPC .................................. 585/435, 449, 446, 467
See application file for complete search history.

(56) References Cited

U.S. PATENT DOCUMENTS

| | | |
|---|---|---|
| 3,626,020 A | 12/1971 | Neuzil et al. |
| 3,702,886 A | 11/1972 | Argauer et al. |
| 3,916,018 A | 10/1975 | Edison et al. |
| 4,377,718 A | 3/1983 | Sato et al. |
| 4,497,972 A | 2/1985 | Neuzil et al. |
| 4,529,828 A | 7/1985 | Antos et al. |
| 4,761,513 A * | 8/1988 | Steacy ........................ 585/467 |
| 5,705,726 A * | 1/1998 | Abichandani et al. ........ 585/481 |
| 6,642,426 B1 | 11/2003 | Johnson et al. |
| 7,060,864 B2 | 6/2006 | Ghosh et al. |
| 7,186,872 B2 | 3/2007 | Juttu et al. |
| 7,279,608 B2 | 10/2007 | Ghosh et al. |
| 7,321,072 B2 * | 1/2008 | Breen et al. ................... 585/467 |

OTHER PUBLICATIONS

International Search Report; International Application No. PCT/US2010/036060; International Filing Date: Feb. 25, 2010; Date of Mailing: Jul. 12, 2010; 3 Pages.
Written Opinion of the International Searching Authority; International Application No. PCT/US2010/036060; International Filing Date: May 25, 2010; Date of Mailing: Jul. 12, 2010; 4 Pages.

* cited by examiner

*Primary Examiner* — In Suk Bullock
*Assistant Examiner* — Sharon Pregler
(74) *Attorney, Agent, or Firm* — Cantor Colburn LLP

(57) ABSTRACT

The present invention is for a process for the alkylation of aromatic compounds, with a shape-selective zeolite catalyst. The process has reactors in series with $C_{8+}$ aromatics being separated from the product stream effluents from each reactor before passing the reactor effluent to the next reactor with an additional input of methanol. The $C_{8+}$ aromatics are separated into para-xylene and other $C_{8+}$ aromatics. This process is applicable for toluene methylation having a molar excess of toluene:methanol. i.e., greater than 1:1, with a shape-selective catalyst of an aluminosilicate zeolite, such as ZSM-5 which has been modified with phosphorus,to produce para-xylene (p-xylene).

17 Claims, 2 Drawing Sheets

AROMATIC ALKYLATION PROCESS

BACKGROUND OF THE INVENTION

1. Field of the Invention

The invention relates generally to a process for the alkylation of aromatic compounds, e.g., toluene methylation, with a zeolite catalyst, e.g., an aluminosilicate zeolite which has been modified to be a shape selective catalyst, said process having reactors in series and more specifically relates to a process to produce para-xylene (p-xylene) by toluene methylation with a shape selective zeolite catalyst in a series of reactors with interstage separation of $C_{8+}$ aromatics.

2. Description of the Prior Art

Toluene methylation (TM) is a catalytic reaction of toluene with methanol to produce xylenes as shown below:

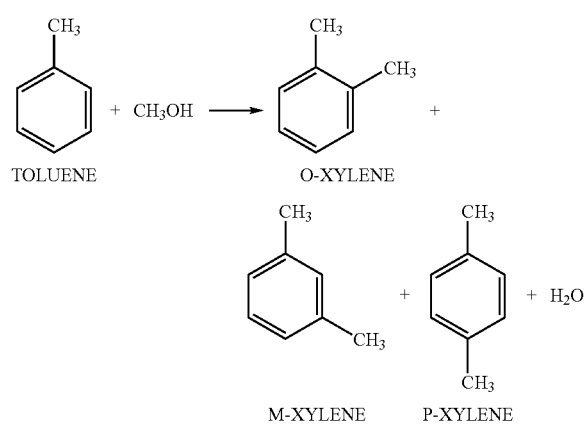

Toluene methylation is an equimolar reaction, i.e., one mole of toluene reacts with one mole of methanol.

Zeolites which are crystalline solids made up of aluminum-substituted $SiO_4$ tetrahedral units joined together to form different ring and cage structures into a crystalline framework can be used as catalyst for toluene methylation. The physical structure of zeolite is very porous with a large internal and external surface area. Zeolites can be shape-selective catalysts due to steric and electronic effects. Shape selective properties can be obtained by modifying the zeolite, e.g., narrowing zeolite pore opening size, inactivation of the external surface of the zeolite or altering zeolite acidity. Deposition of certain compounds or elements on the zeolite can make it more shape selective, e.g., compounds containing iron, zinc, phosphorus, rare earth metal oxides, etc.

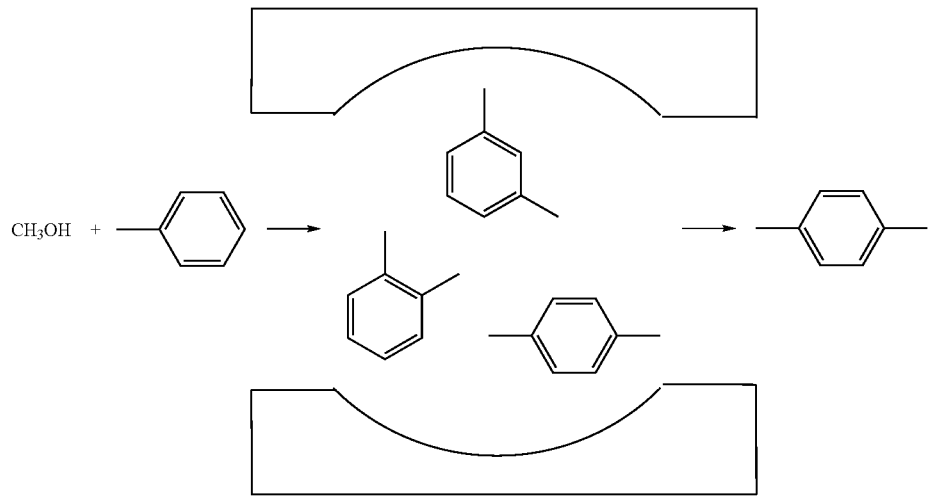

In the synthesis of p-xylene by methylation of toluene, the conversion of toluene and the selectivity of p-xylene, i.e., concentration of p-xylene in the xylene isomers are of commercial importance. Para-xylene (PX) is of particular value as a large volume chemical intermediate in a number of applications being useful in the manufacture of terephthalates which are intermediates for the manufacture of PET. It would be advantageous for a process to produce p-xylene at concentrations of at least 85% or at least 90%.

In addition to the methylation of toluene, many competing side reactions can occur. Methanol may react with itself to form olefins. Toluene can be over-alkylated to form $C_{9+}$ aromatics.

U.S. Pat. No. 4,761,513 discloses a multistage process for alkylation of aromatic hydrocarbons in which the temperatures are controlled by adding the alkylating reactant into each reactor proportionately in both liquid and vapor phase to provide a quench to control temperatures in the reactors. Alkylate product is recovered from the last reaction zone.

U.S. Pat. No. 6,642,426 discloses a process for alkylation of aromatics in a fluidized bed reactor in which a portion of the alkylating reagent is introduced with or near the aromatic reactant and a portion is injected downstream from where the aromatic reactant is introduced, such as into the fluidized bed along the flow axis of the reactor or into a region between two separate discrete fluidized beds.

U.S. Pat. No. 4,377,718 discloses a multistage process for producing p-xylene in a plurality of separate series-connected fixed catalyst layers with toluene being fed with hydrogen into only the first stage and passed successively through each subsequent fixed catalyst layer and the methylating agent being fed into each fixed catalyst layer.

U.S. Pat. No. 7,321,072 discloses a process for producing p-xylene by selective methylation of toluene in a flow reactor at a contact time between a reactant mixture of toluene, methanol and added water and a zeolite catalyst of less than 1 second at a temperature of from 250 to 500° C. The process may be carried out in fixed, moving or fluid catalyst beds, either individually or connected to form multiple bed catalytic reactors. Optionally, in a multiple bed arrangement, additional methanol can be introduced into the reaction mixture between beds to improve conversion.

A process which would increase p-xylene concentration in the mixed-xylene product stream so that separation of p-xylene from o-xylene and p-xylene can be more easily accomplished would be advantageous.

SUMMARY OF THE INVENTION

The present invention is for a method of alkylation of an aromatic in a series of reactors comprising:
a) contacting in a first reactor an aromatic compound and an alkylating agent under reaction conditions suitable for aromatic alkylation in the presence of a shape-selective zeolite catalyst;
b) withdrawing a product stream from the first reactor;
c) separating a stream comprising at least 50% of all $C_{8+}$ aromatics produced in the first reactor from the product stream from the first reactor;
d) introducing additional alkylating agent and the remaining product stream from the first reactor to a second reactor;
e) withdrawing a product stream from a last reactor; and
f) separating para-xylene from the product stream of the last reactor and the separated steam(s) comprising at least 50% of all $C_{8+}$ aromatics produced in the reactor(s).

The $C_{8+}$ aromatics streams may be combined and desired products(s) may be separated out. An example of the aromatic compound is toluene, an example of the alkylating agent is methanol and an example of a desired product is para-xylene. The zeolite catalyst may be a phosphorus-treated zeolite having a phosphorus content of from 0.01 to about 0.15 gram of phosphorus per gram of zeolite and the zeolite may be a ZSM-5-type zeolite. The process of the present invention is run in series, having at least two reactors and having a last reactor from which $C_{8+}$ aromatics are not necessarily separated from the product stream of this last reactor. From about 50% to about 100% of the $C_{8+}$ aromatics is separated from the product stream from each reactor except, optionally, the last reactor. The aromatic compound may be toluene and the alkylating agent may be methanol. To reduce side reactions, the toluene:methanol mole ratio instead of being equimolar, i.e., 1:1, has a molar excess of toluene. i.e., greater than 1:1, and may range from 2:1 to 20:1. Conversion of toluene may range from 5% to 50%.

DESCRIPTION OF EMBODIMENTS OF THE INVENTION

Figure 1:
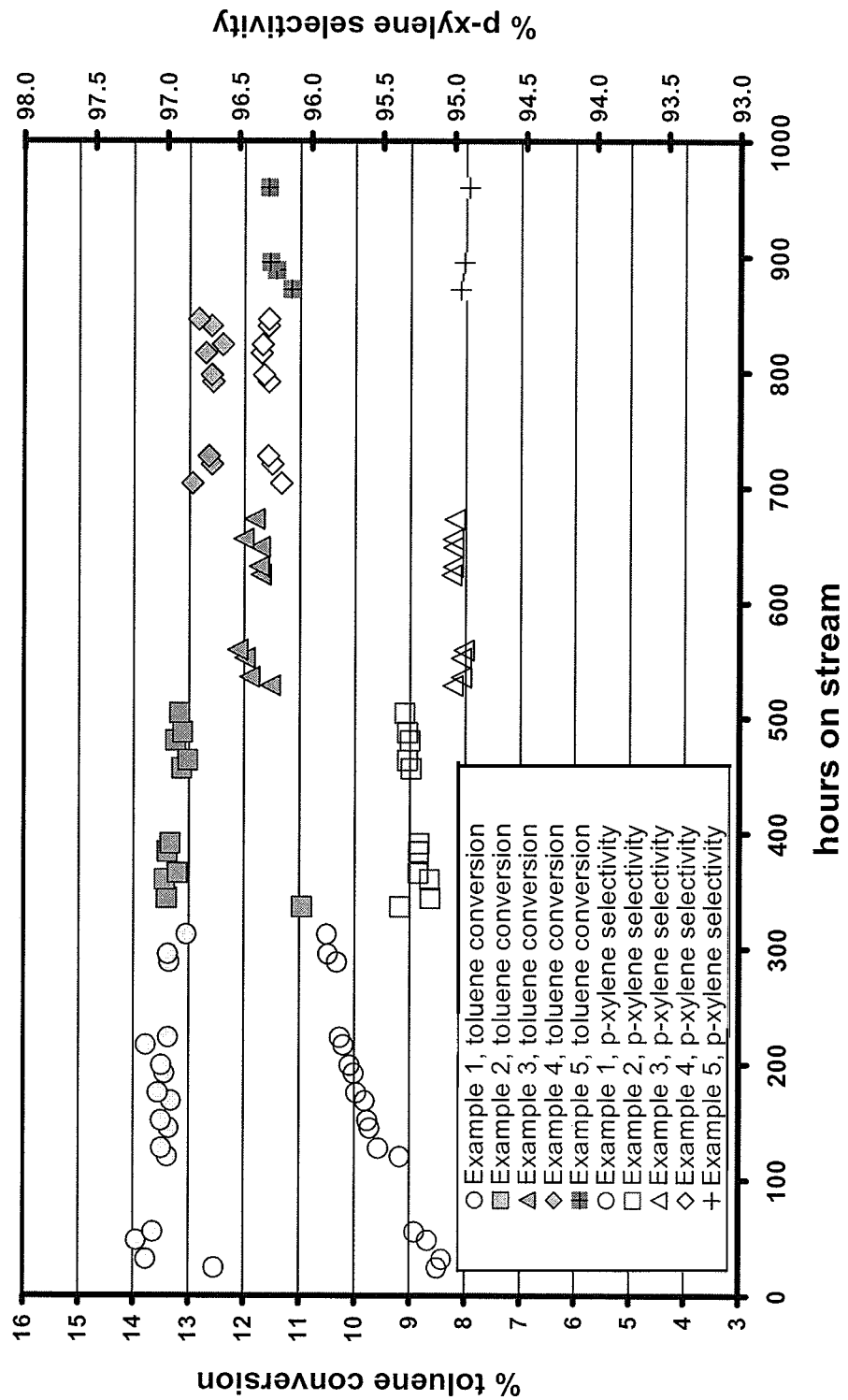
FIG. 1 is a graph of % toluene conversion and % p-xylene selectivity v. hours on stream for Examples 1, 2, 3, 4 and 5.

Toluene methylation is known to occur over zeolite or zeolite-type catalysts, in particular, ZSM-5-type zeolite catalysts. Generally, a thermodynamic equilibrium mixture of ortho (o)-, meta (m)- and para (p)-xylenes is formed from the methylation of toluene. Thermodynamic equilibrium compositions of o-, m-, and p-xylenes may be around 25, 50 and 25 mole %, respectively, at a reaction temperature of about 500° C. Such toluene methylation may occur over at wide range of temperatures, however.

A high purity grade (99+%) p-xylene is desirable for its oxidation to terephthalic acid process. Thus, an increased concentration of p-xylene over equilibrium is desirable.

Zeolite is a crystalline hydrated aluminosilicate that may also contain other metals, such as sodium, calcium, barium, and potassium, and that has ion exchange properties (Encarta® World English Dictionary [North American Edition]© & (P) 2001 Microsoft Corporation). Examples of zeolites are ZSM-5, ZSM-11, ZSM-5/ZSM-11 intermediate, ZSM-12, ZSM-21, ZSM-22, ZSM-23, ZSM-35, ZSM-38, ZSM-48, ZSM-50, MCM-22, Zeolite L, Zeolite Beta and Mordenite which are known in the art. The present invention incorporates modification of zeolites to be shape selective catalysts.

ZSM-5 zeolite is a porous material containing intersecting two-dimensional pore structure with 10-membered oxygen rings. Zeolites with such 10-membered oxygen ring pore structures are often classified as medium-pore zeolites. As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense.

ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of 200 or higher, more particularly from about 250 to about 500 prior to modification. The starting ZSM-5 may be an $NH_4^+$ or $H^+$ form and may contain traces of other cations. Modification of ZSM-5-type zeolite with phosphorus-containing compounds has been shown to provide shape selective properties to the catalyst, yielding significantly greater amounts of p-xylene than the thermodynamic equilibrium value when used in toluene methylation compared to unmodified catalysts. Such modification has been shown to provide selectivity for p-xylenes of greater than 80%.

The ZSM-5-type zeolite may be modified by treating with phosphorus-containing compounds including, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4)_2HPO_4$) may be used as the phosphorus-containing compound to provide a catalyst for toluene methylation with shape selective properties to provide increased p-xylene selectivity. Such modified catalysts may contain phosphorus (P) in an amount of from about 0.01 to about 0.15 g P/g zeolite, more particularly from about 0.02 to about 0.13 g P/g zeolite, and more particularly from about 0.07 g P/g zeolite to about 0.12 g P/g zeolite, and still more particularly from about 0.09 g P/g zeolite to about 0.11 g P/g zeolite. After phosphorus treatment, the phosphorus-treated zeolite may be dried.

The P-modified ZSM-5 catalyst may be contacted with an appropriate feed of an aromatic hydrocarbon and an alkylating agent under alkylation reaction conditions to carry out aromatic alkylation. The catalyst has particular application for use in toluene methylation utilizing a toluene/methanol feed. A gas cofeed may also be used. The cofeed gas may include hydrogen or an inert gas. As used herein, the expression "alkylation feed" is meant to encompass the aromatic compound and the alkylating agent. As used herein, the expression "methylation feed" is meant to encompass the feed of toluene and methanol.

In addition to any cofeed gas, water that may be in the form of steam may also be introduced into the reactor as cofeed along with the alkylation feed. The water or steam used for the methylation reaction may be introduced with or without hydrogen or inert gas as cofeed with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed is described in U.S. Pat. No. 7,060,864 issued Jun. 13, 2006, and entitled "Toluene Methylation Process," and in U.S. Pat. No. 7,279,608 issued Oct. 9, 2007, as a continuation-in-part application entitled "Toluene Methylation Process with Increased Methanol Selectivity", both of which are herein incorporated by reference.

The reactor pressure for toluene methylation or other aromatic alkylation may vary, but typically ranges from about 10 to about 1000 psig. Reactor temperatures may vary, but typically range from about 400 to about 700° C. Upon introduction of feed into the reactor, the catalyst bed temperature may be adjusted to a selected reaction temperature to effect a desired conversion. The temperature may be increased gradually at a rate of from about 1° C./min to about 10° C./min to provide the desired final reactor temperature. As used in the examples, reactor temperature refers to the temperature as measured at the inlet of the catalyst bed of the reactor.

The reaction may be carried out in a variety of different reactors that are commonly used for carrying out aromatic alkylation reactions. Single or multiple reactors in series and/or parallel are suitable for carrying out the aromatic alkylation. Methanol and/or toluene may be added to the product stream entering the second and subsequent reactors when using multiple reactors in series.

The aromatic alkylation process of the present invention is run in a series of reactor with $C_{8+}$ aromatics, e.g. para-xylene, meta-xylene, ortho-xylene, ethylbenzene and aromatics containing nine or more carbon atoms, being separated from the effluent from the first reactor before passing the first reactor effluent to the second reactor with an additional input of methanol. Similarly, the effluent from the second reactor may be put to a third reactor along with additional methanol (with $C_{8+}$ aromatics being separated from the effluent from the second reactor). The amount of remaining (unconverted) toluene from each reactor will depend on the conversion per pass and, accordingly, the concentration of toluene in the feed will decrease from the first reactor to second, and second to third etc. The streams of $C_{8+}$ aromatics after being separated from the effluent from each reactor may be combined together and separated into a product stream of para-xylene and another stream of the other $C_{8+}$ aromatics, such as meta-xylene, ortho-xylene and ethylbenzene. There at least two reactors in series in the present invention and a last reactor from which $C_{8+}$ aromatics are not necessarily separated from the product stream of this last reactor. The second reactor may be the last reactor or there may be reactor(s) in addition to the first reactor from which $C_{8+}$ aromatics are separated from the reactor(s) product stream. At least 50% of all $C_{8+}$ aromatics produced in the reactor(s) is separated from the product stream from all reactor(s) with, optionally, the exception of the last reactor. The product stream of the last reactor may have para-xylene separated without first separating all $C_{8+}$ aromatics produced in the last reactor. The amount of $C_{8+}$ aromatics separated from the product stream of the reactor(s) may be in the range from about 50% to about 100% or in the range from about 50% to about 75%.

Figure 2:
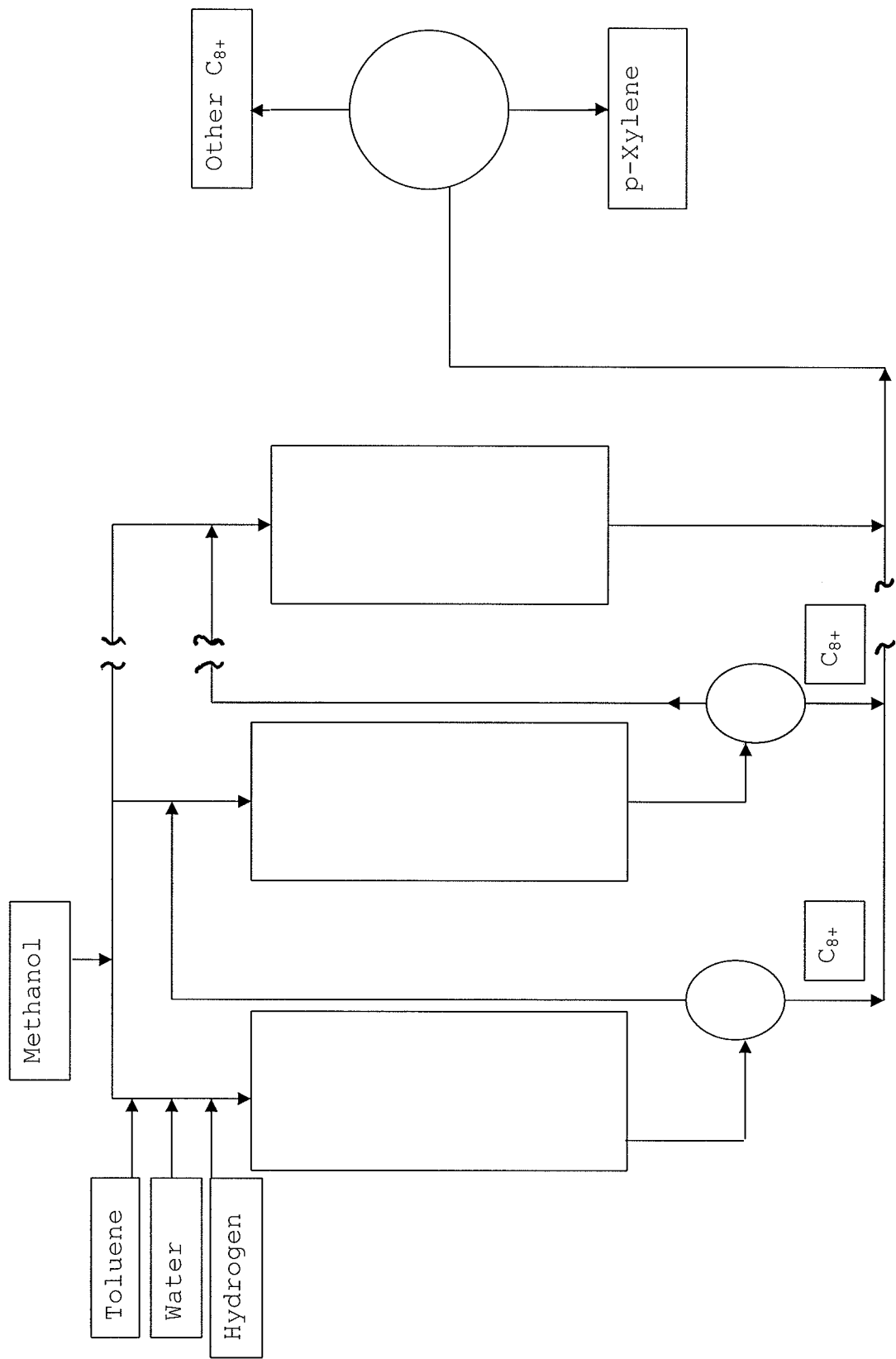
FIG. 2 is a flow diagram of a process for methylation of toluene with reactors in series with intermediate separation of $C_{8+}$ aromatics

One embodiment of the subject invention, as illustrated in FIG. 2, may be characterized as a process which comprises the steps of charging a feed stream containing toluene, methanol, water and hydrogen into a first methylation zone maintained at conditions effective to produce a methylated effluent stream comprising hydrogen, light hydrocarbons, toluene, and $C_{8+}$ aromatics; passing the methylated effluent stream from the first methylation zone into a first separation zone maintained at conditions effective to separate entering hydrocarbons into a first process stream comprising toluene and a second process stream comprising $C_{8+}$ aromatics; charging the first process stream with additional methanol into a second methylation zone maintained at conditions effective to produce a methylated effluent stream comprising hydrogen, light hydrocarbons, toluene, and $C_{8+}$ aromatics; passing the second process stream comprising $C_{8+}$ aromatics into a central separation zone maintained at conditions effective to recover a final product stream comprising a preferred $C_{8+}$ aromatics isomer, such as para-xylene; passing the methylated effluent stream from the second methylation zone into a second separation zone maintained at conditions effective to separate entering hydrocarbons into a third process stream comprising toluene, and a fourth process stream comprising $C_{8+}$ aromatics; passing the fourth process stream comprising $C_{8+}$ aromatics into a central separation zone maintained at conditions effective to recover a final product stream comprising a preferred $C_{8+}$ aromatics isomer, such as para-xylene; having a final reactor into which additional methanol and a process stream comprising toluene which has been separated from the product stream of the penultimate reactor is feed; passing the methylated effluent stream from the first methylation zone into a central separation zone maintained at conditions effective to recover a final product stream comprising a preferred $C_{8+}$ aromatics isomer, such as para-xylene.

Separation of para-xylene from the other isomers is expensive. Interstage separation of $C_{8+}$ aromatics avoids excessive energy cost in the separation of a preferred $C_{8+}$ aromatics isomer from nonpreferred $C_{8+}$ aromatics isomers. There are three commercial techniques to recover para-xylene: fractionation, crystallization and adsorption, which can be used individually or in combinations to lower capital costs.

In fractionation, the reaction product is produced in a gaseous form and is collected and recovered from the reactor outlet stream, such as by condensation. The hydrocarbon liquid is subsequently fractionated using conventional distillation and recovery equipment Selective crystallization at low temperatures for separation and recovery of a preferred $C_{8+}$ aromatics isomer, such as para-xylene, meta-xylene, ortho-xylene, or ethylbenzene, may be a single stage of crystallization, followed by a brief treatment with a wash solvent which is later separated from the desired $C_{8+}$ aromatic isomer can produce, for example, para-xylene of 99.2% purity. This method is further described in U.S. Pat. No. 3,916,018. Higher preferred $C_8$ aromatic isomer purities can be obtained by adding additional stages of crystallization or separating the various types of crystals produced by their physical properties, also described in U.S. Pat. No. 3,916,018.

In the Parex process, liquid-phase adsorption utilizes both x- and y-type zeolites to preferentially adsorb one xylene isomer. A subsequent desorption step is then used to desorb the preferentially absorbed component. The process may be carried out within the temperature range of 40° C. to about 200° C. within a pressure range of from about atmospheric to about 33,000 kPa as described in U.S. Pat. No. 3,626,020. X-type zeolitic adsorbents can be used to recover orthoxylene, as described in U.S. Pat. No. 4,529,828, or ethylbenzene, as described in U.S. Pat. No. 4,497,972.

The ortho-xylene and meta-xylene remaining from the para-xylene separation may be isomerized to produce an equilibrium mixture of xylenes. The ethylbenzene may be isomerized into xylenes or dealkylated to benzene and ethane.

The invention having been generally described, the following examples are given as particular embodiments of the invention and to demonstrate the practice and advantages thereof. It is understood that the examples are given by way of illustration and are not intended to limit the invention, the specification or the claims in any manner.

As used herein, catalytic activity can be expressed as the % moles of the toluene converted with respect to the moles of toluene fed and can be defined by the following formulas:

$$\text{Mole \% Toluene Conversion} = [(T_i - T_o)/T_i] \times 100 \quad (1)$$

where, $T_i$ is the number of moles of toluene fed and $T_o$ is the number of moles toluene unreacted.

As used herein, selectivity for mixed xylenes may be expressed as:

$$\text{Mole \% Mixed Xylene Selectivity} = [X_{tx}/(T_i - T_o)] \times 100 \quad (2)$$

where, $X_{tx}$ is the number of moles of mixed (o-, m- or p-) xylenes in the product.

As used herein, selectivity for p-xylene may be expressed as:

$$\text{Mole \% p-Xylene Selectivity} = (X_p/X_{tx}) \times 100 \quad (3)$$

where, $X_p$ is the number of moles of p-xylene.

As used herein, methanol conversion may be expressed as:

$$\text{Mole \% Methanol Conversion} = [(M_i - M_o)/M_i] \times 100 \quad (4)$$

where, $M_i$ is the number of moles of methanol fed and $M_o$ is the number of moles methanol unreacted.

As used herein, methanol selectivity for toluene methylation may be expressed as:

$$\text{Mole \% Methanol Selectivity} = [X_{tx}/(M_i - M_o)] \times 100 \quad (5)$$

where, $X_{tx}$ is the number of moles of mixed (o-, m- or p-) xylenes, $M_i$ is the number of moles of methanol fed and $M_o$ is the number of moles of unreacted methanol.

EXAMPLES

Catalyst Preparation

P-modified ZSM-5 custom catalyst was made using NH$_4$-ZSM-5 zeolite powder having SiO$_2$/Al$_2$O$_3$ mole ratio between 250 and 300 by treating with P-containing compound and then heating at a maximum temperature of about 550° C. The P/ZSM-5 zeolite was bound with 20% alumina as binder and extruded to make 1/16-inch diameter cylindrical shape catalyst. The extruded catalyst was calcined or heated at a maximum temperature of about 550° C. Analyses of the P-modified ZSM-5 before binding and extruded catalyst are shown in Table 1.

TABLE 1

| Catalyst | Elemental Analysis, wt % | | | | N$_2$ Adsorption | |
|---|---|---|---|---|---|---|
| | Na$_2$O | SiO$_2$ | Al$_2$O$_3$ | P | SA, m$^2$/g | PV, cc/g |
| Powder Catalyst A | <0.04 | 79.2 | 0.5 | 9.4 | 211 | 0.13 |
| Extruded Catalyst A | <0.04 | 63.4 | 20.4 | 7.5 | 243 | 0.17 |

Example 1

Extruded Catalyst A as described above was tested for toluene methylation reaction in a fixed bed, continuous flow type reactor (a ½-inch OD 316-stainless steel tube). A catalyst charge of 5.4 ml (catalyst size: 20-40 mesh) was loaded in the reactor. The catalyst was dried by slowly raising the catalyst bed temperature (about 5° C./min) to 200° C. under hydrogen flow (200 cm$^3$/min) for at least one hour. The catalyst was steamed by introducing water vapor (2.2 mmole/min) with a carrier gas of H$_2$ (459 cm$^3$/min) at 200° C. overnight. A premixed toluene and methanol feed (molar ratio 4.5/1.0), cofeed hydrogen and water were introduced into the reactor at 200° C. The catalyst test conditions are shown in Table 2. The liquid hourly space velocity (LHSV) [based on methylation feed (toluene plus methanol)] was maintained at about 2 hr$^{-1}$ and a cofeed H$_2$ gas was fed and maintained to provide a H$_2$/methylation feed molar ratio of about 8-9. Water was vaporized prior to introduction to the reactor. The H$_2$O/methylation feed molar ratio was 0.8-0.9 and the reactor inlet pressure was about 20 psig. After introducing all feeds and cofeeds into the reactor at 200° C. the catalyst bed inlet temperature was slowly increased to 495° C. The bed inlet temperature was maintained at about 495° C. to monitor toluene conversion and p-xylene selectivity. The feed and product stream (excluding H$_2$ and H$_2$O) analyses are shown in Table A. FIG. 1 shows toluene conversion and p-xylene selectivity at different time on stream. As shown in FIG. 1, the p-xylene selectivity increased from about 95.1 to 95.9% while toluene conversion decreased from about 13.7% to 13.4% during 310 hour on stream before adding C$_{8+}$ aromatics in the feed for Example 2.

TABLE 2

| Test Conditions for Example 1 | |
|---|---|
| Catalyst | A |
| Catalyst Loading | 5.4 ml (4.7 g) |
| Feed, g/h | |
| Toluene | 9.0863 |
| Methanol | 0.6997 |
| Cofeed, g/h | |
| H$_2$ | 1.9773 |
| Water, g/min | 1.8480 |
| Toluene/Methanol Molar Ratio | 4.5/1.0 |
| Catalyst Bed Inlet Temperature | 495° C. |
| Test Duration (hours on stream) | 0 to 312 h |

Example 2

The reactor feed composition was changed after about 312 hour run in Example 1 by adding C$_{8+}$ aromatic products (mixed xylenes, ethyltoluene and trimethylbenzene) that were produced in toluene methylation reaction. Except the change in feed composition no other changes were made to reactor conditions. The test conditions are shown in Table 3. The feed and product stream (excluding H$_2$ and H$_2$O) analyses are shown in Table A. FIG. 1 shows toluene conversions and p-xylene selectivity at different time on stream. As shown in Table A, about 1.45 g (per hour) of C$_{8+}$ aromatics were produced at 295 hour on stream (example 1), and about 49% or 0.71 g (per hour) of the C$_{8+}$ aromatics were added to feed to effect the p-xylene make in the mixed xylene. As shown FIG. 1, the p-xylene selectivity decreased from 95.9% to about 95.3% when $C_{8+}$ including the mixed xylenes added to the feed. The toluene conversions slightly decreased.

TABLE 3

Test Conditions for Example 2

| | |
|---|---|
| Catalyst | A |
| Catalyst Loading | 5.4 ml (4.7 g) |
| Feed, g/h | |
| Toluene | 8.3899 |
| Methanol | 0.7008 |
| % $C_{8+}$ Aromatics (Relative to $C_{8+}$ Produced in Example 1) Cofeed, g/h | 49 |
| H2 | 1.9656 |
| Water, g/min | 1.7100 |
| Toluene/Methanol Molar Ratio | 4.2/1.0 |
| Catalyst Bed Inlet Temperature | 495° C. |
| Test Duration (hours on stream) | 312.4 to 504.2 h |

Example 3

The feed composition was changed after about 504 hour run in Example 2 by adding $C_{8+}$ aromatic products (mixed xylenes, ethyltoluene and trimethylbenzene) that were produced in toluene methylation reaction. Except the change in feed composition no other changes were made to reactor conditions. The test conditions are shown in Table 4. The feed and product stream (excluding $H_2$ and $H_2O$) analyses are shown in Table A. FIG. 1 shows toluene conversions and p-xylene selectivity at different time on stream. As shown in Table A, about 1.45 g (per hour) of $C_{8+}$ aromatics were produced at 295 hour on stream (example 1), and about 76% or 1.1 g (per hour) of the $C_{8+}$ aromatics were added to feed to effect the p-xylene make in the mixed xylene. As shown FIG. 1, the p-xylene selectivity decreased from 95.9% (example 1) to about 95.0% when $C_{8+}$ including the mixed xylenes added to the feed. The toluene conversions decreased due to change in feed composition but remained almost unchanged during the period (time on stream 335 h to 504 h).

TABLE 4

Test Conditions for Example 3

| | |
|---|---|
| Catalyst | A |
| Catalyst Loading | 5.4 ml (4.7 g) |
| Feed, g/h | |
| Toluene | 8.3516 |
| Methanol | 0.6458 |
| % $C_{8+}$ Aromatics (Relative to $C_{8+}$ Produced in Example 1) Cofeed, g/h | 76 |
| H2 | 1.9738 |
| Water, g/min | 1.9020 |
| Toluene/Methanol Molar Ratio | 4.5/1.0 |
| Catalyst Bed Inlet Temperature | 495° C. |
| Test Duration (hours on stream) | 504.2 to 672.5 h |

Example 4

The feed composition was changed after about 672.5 hour run in Example 3; no $C_{8+}$ aromatics were present in the toluene methylation feed. Except the change in feed composition no other changes were made to reactor conditions. The test conditions are shown in Table 5. The feed and product stream (excluding $H_2$ and $H_2O$) analyses are shown in Table A. FIG. 1 shows toluene conversions and p-xylene selectivity at different time on stream. As shown in Tables A and 5, the feed contained no $C_{8+}$ aromatics. With having no $C_{8+}$ aromatics in the feed the p-xylene selectivity increased from about 95% (example 3) to 96% or higher. The toluene conversions decreased due to change in feed composition but remained almost unchanged during the period (time on stream 672.5 h to 840.0 h).

TABLE 5

Test Conditions for Example 4

| | |
|---|---|
| Catalyst | A |
| Catalyst Loading | 5.4 ml (4.7 g) |
| Feed, g/h | |
| Toluene | 9.1253 |
| Methanol | 0.7027 |
| % $C_{8+}$ Aromatics (Relative to $C_{8+}$ Produced in Example 1) Cofeed, g/h | 0 |
| H2 | 1.9686 |
| Water, g/min | 1.8840 |
| Toluene/Methanol Molar Ratio | 4.5/1.0 |
| Catalyst Bed Inlet Temperature | 495° C. |
| Test Duration (hours on stream) | 672.5 to 840.0 h |

Example 5

The feed composition was changed after about 840 hour run in Example 4 by adding $C_{8+}$ aromatic products (mixed xylenes, ethyltoluene and trimethylbenzene) that were produced in toluene methylation reaction. Except the change in feed composition no other changes were made to reactor conditions. The test conditions are shown in Table 6. The feed and product stream (excluding $H_2$ and $H_2O$) analyses are shown in Table A FIG. 1 shows toluene conversions and p-xylene selectivity at different time on stream. As shown in Tables A and 6, about 1.306 g (per hour) of $C_{8+}$ aromatics were produced at 840 hour on stream (example 4), and about 100% or 1.304 g (per hour) of the $C_{8+}$ aromatics were added to feed to effect the p-xylene make in the mixed xylene (see Table A, 888.3 h time on stream). The molar ratio of toluene to methanol was maintained at 4.5 by adjusting their content in the feed (see Table 6). As shown FIG. 1, the p-xylene selectivity decreased from 96.3% (example 4) to about 95.0% when $C_{8+}$ including the mixed xylenes added to the feed. The toluene conversions decreased due to change in feed composition but remained almost unchanged during the period (time on stream 840.0 h to 983.9 h).

TABLE 6

Test Conditions for Example 5

| | |
|---|---|
| Catalyst | A |
| Catalyst Loading | 5.4 ml (4.7 g) |
| Feed, g/h | |
| Toluene | 7.6914 |
| Methanol | 0.5933 |
| % $C_{8+}$ Aromatics (Relative to $C_{8+}$ Produced in Example 4) Cofeed, g/h | 100 |
| H2 | 2.0170 |
| Water, g/min | 1.8240 |
| Toluene/Methanol Molar Ratio | 4.5/1.0 |

TABLE 6-continued

Test Conditions for Example 5

| | |
|---|---|
| Catalyst Bed Inlet Temperature | 495° C. |
| Test Duration (hours on stream) | 840.0 to 983.9 h | tained $C_{8+}$ aromatics (p-xylene, m-xylene, o-xylene, p-ethyltoluene and 1,2,3-trimethylbenzene) at a level of approximately 100% of the amount produced in Example 4. Selectivity to p-xylene decreased from Example 4 (96.30%) to Example 5 (95.01%). A summary of results from Table A for p-xylene selectivity and percent remainder of $C_{8+}$ aromatics for feed to downstream reactors is shown below in Table B.

TABLE A

| | EXAMPLE | | | | | | | | | |
|---|---|---|---|---|---|---|---|---|---|---|
| | 1 | | 2 | | 3 | | 4 | | 5 | |
| Time on Stream, hour | 144.7 | 295.3 | 359.9 | 504.2 | 535.4 | 655.4 | 720.0 | 840.0 | 888.3 | 983.9 |
| Feed Stream, g/h | | | | | | | | | | |
| Methanol | 0.6997 | 0.7014 | 0.6986 | 0.7008 | 0.6458 | 0.6128 | 0.6963 | 0.6902 | 0.5933 | 0.6033 |
| Toluene | 9.0863 | 9.1086 | 8.3642 | 8.3899 | 8.3516 | 7.9251 | 9.0417 | 8.9398 | 7.6914 | 7.8213 |
| p-Xylene | 0 | 0 | 0.6629 | 0.6649 | 1.0292 | 0.9767 | 0 | 0 | 1.2285 | 1.2492 |
| m-Xylene | 0 | 0 | 0.0162 | 0.0163 | 0.0269 | 0.0255 | 0 | 0 | 0.0300 | 0.0305 |
| o-Xylene | 0 | 0 | 0.0097 | 0.0097 | 0.0135 | 0.0128 | 0 | 0 | 0.0150 | 0.0152 |
| p-Ethyltoluene | 0 | 0 | 0.0065 | 0.0066 | 0.0101 | 0.0096 | 0 | 0 | 0.0120 | 0.0122 |
| 1,2,3-Methylbenzene | 0 | 0 | 0.0097 | 0.0097 | 0.0269 | 0.0255 | 0 | 0 | 0.0180 | 0.0183 |
| $C_{8+}$ Aromatics, g/h | 0 | 0 | 0.7050 | 0.7072 | 1.1066 | 1.0501 | 0 | 0 | 1.3035 | 1.3254 |
| Product Stream, g/h | | | | | | | | | | |
| Methane | 0.0049 | 0.0041 | 0.0051 | 0.0045 | 0.0037 | 0.0040 | 0.0040 | 0.0033 | 0.0039 | 0.0039 |
| Ethylene | 0.0685 | 0.0682 | 0.0827 | 0.0768 | 0.0712 | 0.0728 | 0.0613 | 0.0667 | 0.0739 | 0.0713 |
| Propylene | 0.0271 | 0.0281 | 0.0322 | 0.0297 | 0.0263 | 0.0268 | 0.0247 | 0.0267 | 0.0275 | 0.0276 |
| Methanol | 0.0035 | 0.0061 | 0.0061 | 0.0091 | 0.0091 | 0.0148 | 0.0199 | 0.0187 | 0.0206 | 0.0198 |
| Toluene | 7.8295 | 8.0147 | 7.3204 | 7.3726 | 7.4554 | 7.3200 | 7.7300 | 7.7230 | 7.0191 | 7.0867 |
| p-Xylene | 1.3143 | 1.3542 | 1.8860 | 1.8834 | 2.1241 | 2.0917 | 1.2339 | 1.2295 | 2.2109 | 2.2616 |
| m-Xylene | 0.0417 | 0.0396 | 0.0648 | 0.0619 | 0.0775 | 0.0751 | 0.0321 | 0.0321 | 0.0809 | 0.0840 |
| o-Xylene | 0.0190 | 0.0181 | 0.0298 | 0.0289 | 0.0341 | 0.0334 | 0.0157 | 0.0152 | 0.0354 | 0.0369 |
| p-Ethyltoluene | 0.0129 | 0.0132 | 0.0193 | 0.0191 | 0.0207 | 0.0205 | 0.0117 | 0.0120 | 0.0217 | 0.0224 |
| m-Ethyltoluene | 0 | 0 | 0 | 0 | 0 | 0 | 0 | 0 | 0 | 0 |
| o-Ethyltoluene | 0 | 0 | 0 | 0 | 0 | 0 | 0 | 0 | 0 | 0 |
| 1,2,3-trimethylbenzene | 0.0212 | 0.0205 | 0.0084 | 0.0085 | 0.0243 | 0.0248 | 0.0183 | 0.0176 | 0.0187 | 0.0194 |
| 1,2,4-trimethylbenzene | 0 | 0 | 0.0262 | 0.0260 | 0.0271 | 0.0262 | 0 | 0 | 0.0266 | 0.0278 |
| 1,2,3-trimethylbenzene | 0 | 0 | 0 | 0 | 0 | 0 | 0 | 0 | 0 | 0 |
| $C_{10+}$ | 0 | 0 | 0 | 0 | 0 | 0 | 0 | 0 | 0 | 0 |
| $C_{8+}$ Aromatics, g/h | 1.4091 | 1.4456 | 2.0345 | 2.0278 | 2.3078 | 2.2717 | 1.3117 | 1.3064 | 2.3942 | 2.4521 |
| % p-Xylene Selectivity | 95.58 | 95.92 | 95.23 | 95.40 | 95.01 | 95.07 | 96.27 | 96.30 | 95.01 | 94.93 |

These Examples simulate reactors in series and demonstrate the effect of separation of $C_{8+}$ aromatics from intermediate product streams from reactors in series on shape-selectivity of a catalyst used to produce para-xylene in methylation of toluene. Examples 1 and 4 simulate the first reactor in series since only methanol and toluene were fed into the reactor. It should be noted that $C_{8+}$ aromatics (p-xylene, m-xylene, o-xylene, p-ethyltoluene and 1,2,3-trimethylbenzene) were produced. Examples 2, 3 and 5 simulate downstream reactors, i.e., reactors after the first reactor in series with some or none of the $C_{8+}$ aromatics produced in the first reactor removed before feeding to a downstream reactor. Example 2 demonstrates partial removal of $C_{8+}$ aromatics (p-xylene, m-xylene, o-xylene, p-ethyltoluene and 1,2,3-trimethylbenzene) since, in addition to methanol and toluene, the feed contained $C_{8+}$ aromatics (p-xylene, m-xylene, o-xylene, p-ethyltoluene and 1,2,3-trimethylbenzene) at a level of approximately 50% of the amount produced in Example 1. Selectivity to p-xylene decreased from Example 1 (95.92%) to Example 2 (95.23%). In Example 3, the feed contained $C_{8+}$ aromatics (p-xylene, m-xylene, o-xylene, p-ethyltoluene and 1,2,3-trimethylbenzene) at a level of approximately 75% of the amount produced in Example 1. Selectivity to p-xylene further decreased from Example 1 (95.92%) to Example 3 (95.01%). In Example 4, only methanol and toluene were fed into the reactor as in Example 1. Selectivity to p-xylene returned to level of Example 1. In Example 5, the feed contained $C_{8+}$ aromatics (p-xylene, m-xylene, o-xylene, p-ethyltoluene and 1,2,3-trimethylbenzene) at a level of approximately 100% of the amount produced in Example 4. Selectivity to p-xylene decreased from Example 4 (96.30%) to Example 5 (95.01%). A summary of results from Table A for p-xylene selectivity and percent remainder of $C_{8+}$ aromatics for feed to downstream reactors is shown below in Table B.

TABLE B

| Example | p-Xylene Selectivity (%) | | Percent Remainder (%) |
|---|---|---|---|
| 1 | 95.58 | 95.92 | 0 |
| 2 | 95.23 | 95.40 | 49 |
| 3 | 95.01 | 95.07 | 76 |
| 4 | 96.27 | 96.30 | 0 |
| 5 | 95.01 | 94.93 | 100 |

These results show that if reactors in series do not have $C_{8+}$ aromatics (p-xylene, m-xylene, o-xylene, p-ethyltoluene and 1,2,3-trimethylbenzene) separated from the intermediate product streams, p-xylene selectivity decreases. It would be advantageous to remove at least 50% of $C_{8+}$ aromatics (p-xylene, m-xylene, o-xylene, p-ethyltoluene and 1,2,3-trimethylbenzene) from the intermediate product stream of the first and each intermediate reactor, i.e., all reactors except the last reactor in series.

Para-xylene may be used in products such as terephthalic acid, dimethyl terephthalate, polyethylene terephthalate polymer, and the like, which in turn can be used to make synthetic fibers, a high volume multi million dollar industry. The production of para-xylene is a business in which even a small improvement in the process results in improving the cost effectiveness of the large scale economics. A problem associated with the toluene methylation process is that the separation or extraction of aromatics can add significantly to the cost of producing of para-xylene. The separation capacity must accommodate the selectivity of the toluene methylation reaction to para-xylene. Separation of para-xylene as a separate fraction from other aromatic products may require substantial capital investment in additional or larger equipment.

Typical separation procedures, which may be used separately or in combination, include costly fractionation, crystallization and adsorption of p-xylene from other aromatics, some of which may be recycled. Those persons who are skilled in the art appreciate that the expense of the separation process is proportional to the degree of separation required. Because the product produced by the present process has a relatively high amount of para-xylene, 95% or more, separation of para-xylene can be a simple and relatively inexpensive procedure which eliminates or reduces expensive secondary and tertiary treatment procedures. Therefore, significant cost savings are achieved by a process for the production of p-xylene from toluene with improved selectivity to para-xylene while maintaining commercially acceptable conversion levels.

In view of the above considerations, it is clear that catalysts and processes for shape selective hydrocarbon conversion are critical to improving the quality and yield of materials suitable for commercial manufacturing. Accordingly, one of the problems solved by this invention is to overcome limitations in the toluene methylation process by providing a process wherein reactors in series have $C_{8+}$ aromatics separated from the product stream effluents from each reactor before passing the reactor effluent to the next reactor with an additional input of methanol catalyst. This interstage separation process results in a hydrocarbon conversion process with improved selectivity to para-xylene and reduced costs.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A method of alkylation of an aromatic in a series of reactors comprising:
   a) contacting in a first reactor an aromatic compound and an alkylating agent under reaction conditions suitable for aromatic alkylation in the presence of a shape-selective zeolite catalyst;
   b) withdrawing a product stream from the first reactor;
   c) separating a stream comprising at least 50 mole % of all $C_{8+}$ aromatics produced in the first reactor from the product stream from the first reactor;
   d) introducing additional alkylating agent and the remaining product stream from the first reactor to a second reactor;
   e) withdrawing a product stream from a last reactor; and
   f) separating para-xylene from the product stream of the last reactor and the separated steam(s) comprising at least 50 mole % of all $C_{8+}$ aromatics produced in the reactor(s).

2. The method of claim 1 wherein the zeolite is a ZSM-5 zeolite.

3. The method of claim 1 wherein the aromatic compound is toluene.

4. The method of claim 1 wherein the aromatic compound is toluene and the alkylating agent is methanol.

5. The method of claim 4 wherein the toluene:methanol mole ratio is greater than 1:1.

6. The method of claim 5 wherein the toluene:methanol mole ratio is in the range from 2:1 to 20:1.

7. The method of claim 1 wherein the zeolite catalyst comprises a phosphorus-treated zeolite having a phosphorus content of from 0.01 to about 0.15 gram of phosphorus per gram of zeolite.

8. The method of claim 7 wherein the zeolite is a ZSM-5 zeolite.

9. The method of claim 1 additionally comprising reactors in addition to the first and second reactors wherein $C_{8+}$ aromatics are separated from the product stream from each additional reactors except the last reactor; introducing the remaining product stream and additional alkylating agent to a succeeding reactor in series.

10. The method of claim 9 wherein from about 50% to about 75% of the $C_{8+}$ aromatics is separated from the product stream from each reactor except the last reactor.

11. The method of claim 9 wherein at least 50% the $C_{8+}$ aromatics is separated from the product stream from all reactors.

12. The method of claim 1 wherein the streams of $C_{8+}$ aromatics are combined and desired product(s) is/are separated.

13. A method of alkylation of an aromatic in a series of reactors comprising:
   a) contacting in a first reactor toluene and methanol in a mole ratio range from 2:1 to 20:1 under reaction conditions suitable for methylation of toluene in the presence of a phosphorus-modified ZSM-5 catalyst;
   b) withdrawing a product stream from the first reactor;
   c) separating $C_{8+}$ aromatics from the product stream from the first reactor;
   d) introducing additional methanol and the remaining product stream from the first reactor to a second reactor;
   e) withdrawing a product stream from a last reactor;
   f) separating para-xylene from the product stream of the last reactor and the separated steam(s) comprising at least 50 mole % of all $C_{8+}$ aromatics produced in the reactor(s).

14. The method of claim 13 additionally comprising reactors in addition to the first and second reactors wherein $C_{8+}$ aromatics are separated from the product stream from each additional reactors except the last reactor; introducing the remaining product stream and additional alkylating agent to a succeeding reactor in series.

15. The method of claim 14 wherein from about 50 mole % to about 75 mole % of the $C_{8+}$ aromatics is separated from the product stream from each reactor except the last reactor.

16. The method of claim 13 wherein at least 50 mole % of the $C_{8+}$ aromatics is separated from the product stream from all reactors.

17. The method of claim 13 wherein the streams of $C_{8+}$ aromatics are combined with product stream of the last reactor and para-xylene is separated.

* * * * *